United States Patent [19]

Andrade et al.

[11] Patent Number: 4,579,979

[45] Date of Patent: Apr. 1, 1986

[54] METHOD FOR PREPARATION OF ACETALS

[75] Inventors: Juan Andrade, Kleinostheim; Dietrich Arntz, Oberursel; Michael Kraft, Rodenbach; Günter Prescher, Hanau, all of Fed. Rep. of Germany

[73] Assignee: Degussa Aktiengesellschaft, Frankfurt, Fed. Rep. of Germany

[21] Appl. No.: 694,371

[22] Filed: Jan. 24, 1985

[30] Foreign Application Priority Data

Feb. 1, 1984 [DE] Fed. Rep. of Germany ....... 3403426

[51] Int. Cl.⁴ .............................................. C07C 43/30
[52] U.S. Cl. .................... 568/596; 568/594; 568/605; 568/591
[58] Field of Search ................ 568/596, 605, 591, 594

[56] References Cited

U.S. PATENT DOCUMENTS 3,137,738 6/1964 June et al. ........................... 568/596
3,641,163 2/1972 Portwood et al. .................. 568/605

FOREIGN PATENT DOCUMENTS 48-57908 8/1973 Japan.
625131 6/1949 United Kingdom ................ 568/605

*Primary Examiner*—Howard T. Mars
*Attorney, Agent, or Firm*—Beveridge, DeGrandi & Weilacher

[57] ABSTRACT

A method of preparation for acetals utilizing saturated or unsaturated aldehydes, in particular, the preparation of dimethylacetals of acetaldehyde, acrolein and methacrolein. The production of the acetal takes place in a liquid phase in the presence of a solid acid catalyst, such as a strongly acidic ion exchange resin or zeolite. The conversion mixture is extracted by means of water and by means of water insoluble organic solvents. There is obtained not only the desired acetals, but in addition also the unconverted initial quantities of the starting materials by a simple method and with very good yields.

17 Claims, No Drawings

METHOD FOR PREPARATION OF ACETALS

The invention relates to a method for the preparation of acetals through the conversion of aldehydes with alcohols in a liquid phase in the presence of a solid acid catalyst.

It is known to prepare diethylacetal of acrolein wherein the conversion of the acrolein is accomplished with the ethyl ester of ortho formic acid (see Org. Synth. Coll., Vol. 4, 1963, pg. 21). The process described therein yields a favorable yield; however, it is very costly and because of that it is undesired for use on a commercial scale.

It is also known that with the action of alcohols on aldehydes in the presence of catalysts, acetals can be prepared. In particular, these conversions of acrolein may be carried out in the presence of stronge acids, such as sulfuric acid, p-toluolsulfonic acid or trichloroacetic acid in water immiscible organic solvents, such as aliphatic or aromatic, especially halogenated hydrocarbons under continuous removal of the evolved water which forms an azeotropic mixture with the solvent (German Pat. No. 930 752, U.S. Pat. No. 2,691,049). A disadvantage exists with regard to these preparations in that conversion times of more than 10 hours must be utilized. In addition, the conversion does not very often run selectively; there is formed to a considerable extent side products and the yields are, especially in the case of the preparation of dimethylacetal of acrolein, unsatisfactory.

It is known in addition, in the case of the conversion of saturated or unsaturated aliphatic aldehydes with difunctional aliphatic alcohols to use acidic anionic exchange resins as catalysts (U.S. Pat. No. 4,024,159). Acidic ion exchange resins serve likewise for the conversion of saturated aliphatic aldehydes with monofunctional alcohols (see Japanese patent 57908/73). In this method, the conversion runs selectively and conversions can be obtained which are close to the conversion equilibrium values which are obtainable. Although it is envisioned to obtain the acetal in a conventional manner, in particular through the distillation from a conversion mixture, the intended and thereby obtained side reactions, however, result in the fact that only unsatisfactory yields can be expected from this procedure. In addition, the recycling and subsequent usage of the unconverted portions of the original starting material are not taught. To do without the recycling of the materials means, as a result, that the method is not practicable and is undesirable for the carrying out of the process on a commercial scale.

It has now been found that a method for the preparation of acetals by the conversion of aldehydes with alcohols may be carried out in liquid phase in the presence of a solid acidic catalyst, and which is characterized by the fact that:

(a) an aldehyde of the formula:

$$R_1\text{-CHO} \tag{I}$$

wherein $R_1$ is a branched or straight chain alkyl group having 1 to 3 carbon atoms or alkenyl group with 2 or 3 carbon atoms,
is reacted with an alcohol of the formula:

$$R_2\text{-OH} \tag{II}$$

in which $R_2$ is an alkyl group of 1 or 2 carbon atoms, wherein the reaction is carried out in the presence of a solid acidic catalyst to form a conversion mixture;

(b) the conversion mixture after removal of the catalyst is extracted by means of water and by means of water insoluble organic solvents; and (c) the resulting acetals as well as the unconverted initial quantities of aldehyde and alcohol are obtained from the extract.

This method not only achieves efficient conversions but is also outstandingly selective. The resulting acetals as well as the unconverted starting portions of aldehyde and alcohol are removed by simple means from the conversion mixture and are obtained in very good yields.

For the conversion in accordance with the present invention, the designated aldehydes that can be used are for example propionaldehyde, n-butyraldehyde, isobutyraldehyde, crotonaldehyde and especially acetaldehyde, acrolein and methacrolein. Suitable alcohols are ethanol and in particular methanol.

The method of the present invention serves particularly well for the preparation of acetals of the formula:

$$R_1\text{-CH-(OR}_2)_2 \tag{III}$$

in which $R_1$ and $R_2$ have the same meaning as set forth in Formulae (I) and (II) above. In particular, the method is suitable for the preparation of dimethylacetals of acetaldehyde, acrolein and methacrolein.

The proportional relationship of the aldehyde to alcohol can be varied widely as desired. In general, it is desirable that the alcohol be present in an amount in excess of the stoichiometric quantity need for the reaction.

The conversion is carried out in the presence of a solid acidic catalyst. As examples thereof, the following are particularly suitable: acidic, in particular strongly acidic, ionic exchange resins or strongly acidic zeolites. Particularly suitable are the sulfonated styrene-divinylbenzene copolymers known in the art for strongly acid ion-exchange purposes; see Kirk-Othmer, Encyl. Chem. Tech., 2nd Ed., Vol. 11, page 874; 3rd Ed., Vol. 13, page 686. Any of such materials may be used for this purpose. The proportional relationship of catalysts to aldehyde is arranged in accordance with the conventional art of catalysts. Of the ion exchange resin, it is useful to use at least 1.0 g, especially at least 5.0 g and of the zeolites at least 0.5 g, especially at least 1.0 g, for every mol of aldehyde is used.

For the conversion, it is fundamental that the temperatures that are used range up to the boiling point of the conversion mixture. Particularly useful is the temperature approximately between 0° to 50° C. and especially between 10° to 30° C.

The resulting conversion mixtures that are obtained as a result of the conversion of the aldehyde with the alcohol contain in addition to the resulting acetals, portions of unconverted initial aldehyde and alcohol. According to the invention, after removal of the catalysts therefrom, the conversion mixture is extracted by means of water and by means of inert water insoluble organic solvents. In this procedure, the acetals are taken up by the organic solvents and the aldehydes and particularly the specific aldehydes in which $R_1$, according to Formula I, is an alkyl or alkenyl group with 2 carbon atoms as well as the alcohol is preferentially taken up by the water.

As to which organic solvents can be used, this is determined, as necessary, according to the properties of the resulting substance in the conversion mixture. As solvents, there can be mentioned aliphatic or aromatic hydrocarbons, optionally, halogenated hydrocarbons. Preferred are the aliphatic hydrocarbons that have 5 to 14 carbon atoms. Particularly useful solvent materials are for example, benzol, toluol, xylol, methylenechloride, trichloromethane, tetrachloromethane, and chlorobenzol, in particular, n-pentane, n-heptane and n-octane.

The water and the organic solvent can be usefully introduced in those amounts so that in the extraction, the resulting acetal is taken up as completely as possible with the organic solvent and herewith preferably completely separated from the unconverted initial quantities of aldehyde and alcohol. In the cases wherein the extraction is carried out in a continuous manner in an countercurrent stream, it is altogether useful for the volume portion of the conversion mixture to be set at 1 to 4 volume parts of water and 1 to 3 volume parts organic solvent.

The alcohols and aldehydes which are extracted with the water are suitably separated through distillation of the water. They can be immediately renewed for introduction into the production of the acetal.

By means of the organic solvent, the certain quantities of the initial aldehyde and alcohol can be extracted in general in addition to the acetals. Also, the obtaining of these substances can be carried out in a useful manner through distillation. In this case, it is particularly desirable to choose organic solvents which have distinctly higher boiling points than do the acetals, aldehydes and alcohols. In those cases where the acetals have the same boiling point or equivalent boiling points as the aldehydes and alcohols and it is therefore not possible to remove these acetals from these substances through distillation, it is useful to add so much water in the extraction that the aldehyde and the alcohol are completely taken up by the water.

The following examples serve to illustrate the invention without limiting it in any respect.

EXAMPLE 1

Into a loop reactor, there was introduced on an hourly basis a 169.3 g (3.02 mol) acrolein which is mixed with 189.1 g (5.91 mol) methanol in a concurrent stream. This stream is then mixed with 117.1 g (2.09 mol) acrolein and 450.9 g (14.1 mol) methanol, both having been recovered from the conversion mixture. In the circulation system of the reactor, the mixture streams through a zone which is filled with 100 g of strongly acidic ionic exchange resin (Dowex MSC-1) which is a sulfontated styrene divinylbenzene copolymer. The temperature in the reactor is held at 17° C. and the average dwell time was 2.3 hours. The conversion mixture was then drawn out of the reactor in a concurrent stream and led to the middle of a pulsating extraction column of 25 cm inside width and 400 cm height containing 80 sieves. Into the column, there was introduced on an hourly basis from above 1810 g water and from the bottom 810 g n-octane. The temperature in the column was 20° C. The phases which are withdrawn from the column at the top and at the bottom were fractionally distilled. Herewith there was removed on an hourly basis from the upper phase 290 g (2.84 mol) acrolein-dimethylacetal.

In addition, there was obtained on an hourly basis from the upper phase 6.0 g acrolein and from the lower phase 111.1 g acrolein and 450.9 g methanol are recovered. It was then determined that 59.1% of the total hourly introduced 286.4 g acrolein was converted. The recovered acrolein and methanol were led back to the loop reactor. With the distillation of the upper phase, there was obtained as a distillate octane and with the distillation of the lower phase, water was obtained. The octane and the predominant portion of the water were led back to the extraction column and the remaining water was discarded. The acetal obtained was 98%. The boiling point was 89° to 90° C. The yield calculated on the basis of the converted acrolein was 94% and with that, the selectivity was 94%.

EXAMPLE 2

The process according to Example 1 was carried out, however, 184 g (4.2 mol) acetaldehyde and 275 g (8.6 mol) methanol together with the recovered initial quantities of acetaldehyde and methanol from the conversion mixture were introduced on an hourly basis. The temperature of the reactor was held at 18° C., the average dwell time was 3.8 hours and the conversion mixture was led to an extraction column which is charged hourly with 1530 g water and 1510 g n-octane. Every hour there was recovered from the organic phase 9 g acetaldehyde, 2 g methanol and 367 acetaldehyde-dimethylacetaldehyde and from the aqueous phase, 36 g methanol and 43 g acetaldehyde. Consequently, the conversion was 76% of the total acetaldehyde on an hourly basis. The recovered acetal was 98.5%. The boiling point was 64° to 65° C. The yield, calculated based on the converted acetaldehyde, was 98% and the selectivity was 98%.

EXAMPLE 3

There was mixed together 113 g (2 mol) acrolein with 257 g (8 mol) methanol and 5 g of a strongly acidic ionic exchange resin (Dowex MSC-1). The mixture was stirred for 2.5 hours at 15° C. Then, the ion exchange resin was filtered off. The remaining conversion mixture was extracted using 300 ml water and 250 ml n-pentane. The pentane phase was fractionally distilled. At 88° to 90° C., there was recovered 111 g acrolein-dimethylacetal. The acetal was 98% pure. Accordingly, the amount of yield calculated on the basis of the charged acrolein was 53%. The aqueous phase was also fractionally distilled and with that 44 g acrolein and 175 g methanol was obtained. According to that, 61% of the introduced acrolein was converted. For 87% of the converted acroleins, acetal was obtained. The selectivity was therefore 87%.

EXAMPLE 4

There was mixed together 1.05 kg (15 mol) methacrolein with 2.4 liters (60 mol) methanol and 37 g strongly acidic ion exchange resin (Dowex MSC-1). The mixture was stirred for 2 hours at 15° C. Thereafter, the ion exchange resin was filtered off. The residual mixture was extracted with about 2000 ml water and n-pentane. The pentane phase was then fractionally distilled. As a result, there was obtained 680 g methacrolein-dimethylacetal, representing 38% yield calculated on the introduced methacrolein. In addition, there was obtained from the pentane phase, 619 g methacrolein.

According to that, there was obtained a conversion of 41% based on the introduced methacrolein. The acetal was accordingly obtained with a 91% selectivity. With the fractional distillation of the aqueous phase, there was obtained 1850 ml 97% methanol.

EXAMPLE 5

The process was carried out in accordance with Example 3; however, a mixture was introduced formed of 88 g (2 mol) acetaldehyde and 256 g (8 mol) methanol with 10 g of the same ionic exchange resin. The mixture was held for 2 hours at 20° C. and after removal of the ion exchange resin, it was extracted with 300 ml n-heptane and 200 ml water. The yield of the acetaldehyde-dimethylacetal, calculated on the basis of the introduced acetaldehyde, amounted to 73%. The boiling point of the acetal was 64 to 65° C. In addition, there was obtained 22 g acetaldehyde and 159 g methanol. Consequently, the acetal was obtained with a 98% selectivity calculated on the basis of the converted acetaldehyde.

EXAMPLE 6

The procedure of Example 3 was followed; however, the mixture was 88 g (2 mol) acetaldehyde and 192 g (6 mol) methanol with 2 g H-Mordenit as the catalyst. The mixture was held for 3 hours under reflux at the boiling point and after removal of the catalyst, it was extracted at 20° utilizing 300 ml n-octane and 400 ml water. The yield of the acetaldehyde-dimethylacetal, calculated on the basis of the introduced acetaldehyde, amounted to 56%. The boiling point of the acetal was 64 to 65° C. In addition, there was obtained 30 g acetaldehyde and 109 g methanol. Consequently, the acetal was obtained with the selectivity of 86% calculated on the converted acetaldehyde. H-Mordenite is a specific member of a general class of zeolites of the mordenite type. This is produced by ion exchange of an alkali metal zeolite with ammonium ions with subsequent heating of the ion exchanged zeolite according to known techniques. See Kirk-Othmer, Vol. 5, pp. 35–36; Vol. 15, pp. 638–669, 3rd Ed.

EXAMPLE 7

The procedure according to Example 3 was followed except that a mixture was used formed of 116 g (2 mol) propionaldehyde and 257 g (8 mol) methanol with 10 g of the ionic exchange resin. The mixture was held at 50° for 30 minutes and after removal of the ion exchange resin was extracted with 400 ml n-octane and 200 ml water. The yield of the propionaldehyde-dimethylacetal, calculated based on the introduced propionaldehyde, amounted to 50%. The boiling point of the acetal was 87°. In addtion, there was obtained 56 g propionaldehyde and 191 g methanol. Accordingly, the acetal was obtained with 97% selectivity, based on the converted propionaldehyde.

EXAMPLE 8

The procedure according to Example 3 was followed except that the mixture was 88 g (2 mol) acetaldehyde and 128 g (4 mol) methanol with 10 g of the ionic exchange resin. The mixture was held at 20° C. for 1.5 hours and after removal of the ion exchange resin, it was extracted with 300 ml n-octane and 400 ml water. The yield of the acetaldehyde-dimethylacetal, calculated on the introduced acetaldehyde, amounted to 63%. The boiling point of the acetal was 64.5° C. In addition, there was obtained 30 g of acetaldehyde and 43 g methanol. Consequently, the acetal was obtained with 95% selectivity, based on the converted acetaldehyde.

EXAMPLE 9

The procedure according to Example 3 was followed except that the mixture was 88 g (2 mol) acetaldehyde and 257 g (8 mol) methanol with 2 g of the ion exchange resin. The mixture was held at 10° C. for 5.5 hours and after removal of the ion exchange resin was extracted with 350 ml toluol and 300 ml water. The yield of the acetaldehyde-dimethylacetal, calculated on the basis of the introduced acetaldehyde, amounted to 77%. The boiling point of the acetal was 64.5° C. In addition, there was obtained 20 g acetaldehyde and 169 g methanol. Consequently, the acetal was obtained with 99% selectivity, based on the converted acetaldehyde.

EXAMPLE 10

The procedure in Example 3 was followed except that the mixture was 88 g (2 mol) acetaldehyde and 369 g (6 mol) ethanol with 10 g of the ion exchange resin. The mixture was held at 20° for 1.5 hours and after removal of the ion exchange resin, it was extracted with 400 ml n-nonane and 330 ml water. The yield of the acetaldehyde-diethylacetal, calculated based on the introduced acetaldehyde, amounted to 57%. The boiling point of the acetal was 118° C. In addition, there was obtained 35 g acetaldehdye and 256 g ethanol. Consequently, the acetal was obtained with the selectivity of 94%, based on the converted acetaldehyde.

The acidic ion exchange resins and acidic zeolites are known in the art and any suitable ones may be used for purposes of the invention so long as they contain strongly acidic groups; see in this regard Kirk-Othmer, Encyclopedia of Chemical Technology, 3rd Edition, Vol. 9, p. 296 et seq. and Vol. 15, p. 652 et seq.

Further modifications and variations of the invention will be apparent to those skilled in the art based on the foregoing detailed description thereof and are intended to be encompassed by the claims appended hereto.

The German priority application P 34 03 426.9 is relied on and incorporated herein by reference.

We claim:

1. A method for the preparation of acetals comprising reacting an aldehyde with an alcohol in a liquid phase in the presence of a solid acidic catalyst, said aldehyde being represented by the structural formula:

$R_1-CHO$ wherein
$R_1$ is a branched or straight chain alkyl of 1 to 3 carbon atoms or alkenyl having 2 or 3 carbon atoms, said alcohol having the structural formula:

$R_2-OH$ wherein
$R_2$ is an alkyl group having 1 or 2 carbon atoms, carrying out the reaction between the aldehyde and the alcohol in the presence of a solid acidic catalyst removing the catalyst material and extracting the reaction mixture with water and a water insoluble organic solvent obtaining from the extract so produced the acetal as well as unconverted portions of the aldehyde and alcohol.

2. The method according to claim 1, wherein the catalyst is a strongly acidic ion exchange resin or a strongly acidic zeolite.

3. The method according to claim 1, wherein the organic solvent is an aliphatic hydrocarbon having 5 to 14 carbon atoms.

4. The method according to claim 2, wherein the solvent is an aliphatic hydrocarbon having 5 to 14 carbon atoms.

5. The method according to claim 1, wherein acetaldehyde and methanol are reacted together.

6. The method according to claim 2, wherein acetaldehyde and methanol are reacted together.

7. The method according to claim 1, wherein acrolein is reacted with methanol.

8. The method according to claim 2, wherein acrolein is reacted with methanol.

9. The method according to claim 1, wherein methacrolein is reacted with methanol.

10. The method according to claim 2, wherein methacrolein is reacted with methanol.

11. The method according to claim 2, wherein the ion exchange resin is used in the proportion of at least 1 g per mol of aldehyde.

12. The method according to claim 2, wherein the zeolite is used in the amount of at least 0.5 g per mol of aldehyde.

13. The method according to claim 1, wherein the alcohol is used in excess of the stoichiometric amount required for the reaction.

14. The method according to claim 2, wherein the reaction mixture is circulated through a zone containing strongly acidic ion exchange resin for several hours.

15. The method according to claim 1, wherein the water used for extracting the reaction mixture is present in the amount of 1 to 4 volume parts of water and the water insoluble organic solvent is present in the amount of 1 to 3 volume parts organic solvent.

16. A method for the preparation of acetals comprising:

reacting an aldehyde with an alcohol in a liquid phase in the presence of a solid acidic catalyst, wherein the aldehyde is represented by the structural formula:

$R_1\text{-CHO}$ wherein $R_1$ is a branched or straight chain alkyl of 1 to 3 carbons atoms or alkenyl having 2 or 3 carbons atoms, wherein said alcohol has the structural formula:

$R_2\text{-OH}$ wherein $R_2$ is an alkyl group having 1 or 2 carbon atoms, reacting said aldehyde and said alcohol in the presence of a solid acidic catalyst to obtain a conversion mixture containing acetal and any unconverted akdehyde and alcohol, removing the conversion mixture from the presence of the solid acidic catalyst, contacting said conversion mixture with water and with a water insoluble organic solvent under conditions of extraction whereby the acetal which is present in the conversion mixture is perferentially taken up by the said organic solvent and any unconverted initial aldehyde and alcohol is preferentially taken up by the water and thereafter recovering said acetal from the organic phase.

17. The method according to claim 16 wherein the acetal is recovered as a product by a fractional distillation.

* * * * *